(12) United States Patent
Tellenbach et al.

(10) Patent No.: US 9,108,055 B1
(45) Date of Patent: Aug. 18, 2015

(54) SYSTEM FOR ELECTRICAL MUSCLE AND NERVE STIMULATION IN AQUEOUS MEDIA

(71) Applicants: Vincent Tellenbach, Sion (CH); Steeve Rodriguez, Volleges (CH)

(72) Inventors: Vincent Tellenbach, Sion (CH); Steeve Rodriguez, Volleges (CH)

( * ) Notice: Subject to any disclaimer, the term of this patent is extended or adjusted under 35 U.S.C. 154(b) by 65 days.

(21) Appl. No.: 14/179,390

(22) Filed: Feb. 12, 2014

(51) Int. Cl.
*A61N 1/00* (2006.01)
*A61N 1/36* (2006.01)

(52) U.S. Cl.
CPC ........ *A61N 1/36014* (2013.01); *A61N 1/36003* (2013.01)

(58) Field of Classification Search
CPC .............. A61N 1/328; A61N 1/36021; A61N 1/36014; A61N 1/40; A61N 1/0404; A61N 1/0472; A61N 1/0452–1/0468
See application file for complete search history.

(56) References Cited

U.S. PATENT DOCUMENTS

| | | |
|---|---|---|
| 584,957 A | 6/1897 | Patten |
| 647,006 A | 4/1900 | Maggiorani |
| 710,933 A | 10/1902 | Zweibel |
| 1,636,568 A | 7/1927 | Kennedy |
| 1,908,688 A | 5/1933 | Call |
| 2,240,504 A | 5/1941 | Landauer |
| 2,263,205 A | 11/1941 | Conrad |
| 2,344,990 A | 3/1944 | Landauer |
| 2,347,915 A | 5/1944 | Landauer |
| 2,375,575 A | 5/1945 | Morland et al. |
| 2,420,669 A | 5/1947 | Landauer |
| 2,580,232 A | 12/1951 | Landauer |
| 3,083,712 A | 4/1963 | Keegan, Jr, |
| 3,516,413 A | 6/1970 | McDonald et al. |
| RE32,091 E | 3/1986 | Stanton |
| 4,712,558 A | 12/1987 | Kidd et al. |
| 4,846,181 A | 7/1989 | Miller |
| 4,850,956 A | 7/1989 | Bontemps |
| 4,954,922 A | 9/1990 | Caus et al. |
| 5,048,522 A | 9/1991 | Petrofsky |
| 5,158,081 A | 10/1992 | McWhorter et al. |
| 5,197,459 A | 3/1993 | Henkin et al. |
| 5,339,804 A | 8/1994 | Kemp |
| 5,350,415 A | 9/1994 | Cywinski |
| 5,647,826 A | 7/1997 | Butler |
| 5,741,317 A | 4/1998 | Ostrow |
| 6,026,327 A * | 2/2000 | Dervieux ........................ 607/46 |
| 6,249,706 B1 * | 6/2001 | Sobota et al. ................. 607/115 |
| 6,436,060 B1 | 8/2002 | Talish |
| 6,493,588 B1 | 12/2002 | Malaney et al. |
| 6,701,189 B2 | 3/2004 | Fang et al. |
| 7,117,034 B2 | 10/2006 | Kronberg |
| 7,241,250 B1 | 7/2007 | French et al. |
| 7,341,597 B2 | 3/2008 | Tucek |
| 7,740,650 B2 | 6/2010 | Brogan et al. |
| 7,819,007 B2 | 10/2010 | Brooks et al. |
| 7,837,719 B2 | 11/2010 | Brogan et al. |
| 7,883,533 B2 | 2/2011 | Tucek |
| 7,885,708 B2 | 2/2011 | Shanks et al. |
| 7,998,031 B2 | 8/2011 | Dumke et al. |
| 8,165,695 B2 | 4/2012 | DiUbaldi et al. |

(Continued)

*Primary Examiner* — Michael Kahelin
*Assistant Examiner* — Mallika D Fairchild
(74) *Attorney, Agent, or Firm* — John P. McGonagle (57) ABSTRACT

A wand for transmitting an electrical pulse train to a patient in an aqueous medium is provided. The wand has transmitting electrodes positioned adjacent the skin of a patient directly over the treated muscle or over the nerve pathway leading to the muscle. An inert protective grid is placed over each electrode to insure separation between the electrode and patient. The wand is self-contained and sealed blocking all fluids from its interior.

6 Claims, 10 Drawing Sheets

(56) References Cited

U.S. PATENT DOCUMENTS

| | | |
|---|---|---|
| 8,190,262 B2 | 5/2012 | Gerber et al. |
| 8,219,202 B2 | 7/2012 | Giftakis et al. |
| 8,285,381 B2 | 10/2012 | Fahey |
| 8,340,733 B2 | 12/2012 | Heikkinen et al. |
| 8,340,771 B2 | 12/2012 | Thimineur et al. |
| 8,340,786 B2 | 12/2012 | Gross et al. |
| 8,494,658 B2 | 7/2013 | Crowe et al. |
| 2005/0203585 A1 | 9/2005 | Hairfield, Sr. |
| 2006/0063963 A1 | 3/2006 | Brunelle et al. |
| 2008/0087288 A1 | 4/2008 | Wun |
| 2010/0262202 A1 | 10/2010 | Brogan et al. |
| 2012/0165710 A1* | 6/2012 | Nichols .......................... 601/72 |

\* cited by examiner

MOBILE PHONE

COMPUTER

REMOTE CONTROL

FIGURE 9

FIGURE 10

SYSTEM FOR ELECTRICAL MUSCLE AND NERVE STIMULATION IN AQUEOUS MEDIA

CROSS-REFERENCE TO RELATED APPLICATIONS

Applicant claims the priority benefits of U.S. Provisional Patent Application No. 61/763,625, filed Feb. 12, 2013.

BACKGROUND OF THE INVENTION

This invention relates generally to a method and apparatus for effecting therapy on a patient. More particularly, the present invention provides for electrical stimulation of muscles and nerves in aqueous media for the purpose of alleviating a broad range of medical conditions, as well as for specific non-medial objectives.

The number of medical applications that use electrical stimulation is large and covers virtually every living body component. These applications include prevention of muscle atrophy, promotion of wound healing, prevention of venous thrombosis, alleviation of both chronic/acute pain and prevention of incontinence to name but a few. Electrical stimulation is also wide-spread for such non-medical objectives as muscle training, muscle toning, improving muscle endurance, and muscle relaxation. These objectives are likewise attained by the present invention.

Electrical stimulation of muscles and nerves is well established in medicine and physical therapy with a history dating back to mid-1850's. Such stimulation is currently achieved by applying electrodes to: the skin at the point(s) of desired electrical stimulation; and/or through insertion of electrical probes into body cavities, and/or through surgical insertion of electrodes.

Aquatic therapy are programs using mechanical and thermal characteristics of water during partial or complete immersion in combination with the effects of movement. It evokes short-term and long-term adaptational mechanisms of a person with a deranged biological system, using specific stimuli to create biological and thus therapeutic effects. Aquatic physiotherapy is physiotherapy which uses more than one of the unique properties of water for therapeutic rehabilitation. Prior art aquatic therapy deals primarily with devices that enable therapists or patients to more effectively treat medical or non-medical conditions mechanically or ergonomically.

Early attempts to combine electrical stimulation of muscles and nerves in aqueous media treatment were provided through galvanic bath electrotherapy. This is a treatment modality in which patients are immersed in a hot bath (e.g., 34 degree Celsius) and a weak electric current is applied to the bath and passes through the patient's body. Galvanic bath therapy is normally administered for fifteen minutes. The historic targets of galvanic bath therapy have been degenerative diseases such as inflammatory arthritis and joint problems. The direct, constant current used in galvanic bath therapy, however, is generally too weak to maintain force output and is not able to produce tetanic muscle contraction since muscle responses typically occur only when current is turned on and off.

Aquatic electrotherapy prior art that results in effective tetanic electrical stimulation, i.e., electrical stimulation that treats indications approved by the U.S. Drug and Food Administration (FDA) has not been found.

SUMMARY OF THE INVENTION

It is the object of the present invention to provide a system for electric stimulation in an aqueous environment. Stimulation in this manner is simpler, more comfortable for patients, provides better access to specific parts of the body and is more efficient for the medical and non-medical professionals (who administer the electric stimulation) and users in general.

To obtain such muscle contractions or nerve response, a special kind of electrical stimulation device is required. This electric stimulation device and the method of its application are the subjects of this present invention.

The present invention uses short bursts of electrical impulses of high energy and pre-set duration; the impulse bursts have modulated intensities and/or time duration.

A primary object of the present invention is to provide an electric stimulation device that enables safe, tetanic muscle contractions in an aqueous environment.

A secondary object of the present invention is to provide an electric stimulation device that generates and delivers electrical impulses that trigger strong, effective tetonic muscle contractions or nerve responses in a stimulated individual.

Another object of the present invention is to provide an electric stimulation device, in which the delivered electrical impulses are pain-free, even comfortable, to the patient or user.

Another object of the present invention is to provide an electric stimulation device and method for stimulating muscles or nerves by using effective, pre-selected electrical impulses that are stored using internal memory.

An object of the present invention is also to provide an electric stimulation device in which the stored sequences of impulses are associated with pre-determined and unique indications and conditions.

Yet another object of the present invention is to provide an electric stimulation device in which stored impulse sequences are designed specifically for targeted medical or non-medical treatment applications.

Another object of the present invention is to provide an electric stimulation device that may be safely operated by medical and non-medical users.

Another object of the present invention is to provide an electric stimulation method and a device, wherein the generated electrical impulses are delivered to the patient or user by a sealed device containing two electrically conductive electrodes.

Another object of the present invention is the use of radio frequency (RF), Wi-Fi or Bluetooth communications to deliver the electrical stimulation impulses by the present invention device.

Another object of the present invention is to provide an electric stimulation device that automatically stops electrical stimulation signals if/when irregular or abrupt motion is detected.

A further object of the present invention is to provide an electric stimulation device that is simple and safe to use.

A further object of the present invention is to provide a disposable insert into the device that enables use by multiple patients.

A still further object of the present invention is to provide an electric stimulation device that is cost effective for both professionals and users.

The present invention provides a system for stimulation of muscle and nerves that may comprise: (a) a device capable of providing electrical stimulation in varied aqueous media; (b) a device capable of storing accumulated treatment data; (c) a self-contained, portable device that incorporates all required components for aqueous stimulation; (d) a device that incorporates only programs, data collection and communication capabilities; (e) wearable garments that incorporate all required components for electrical stimulation in an aqueous medium; and (f) a disposable insert that enables multiple users for the self-contained, portable device.

The system and device described in the present invention enables medical professionals, such as doctors and clinical therapists, and non-medical professionals, such as athletic trainers or individuals, to safely and effectively merge the benefits of electrical stimulation and aquatic therapy in various aqueous media.

The present invention may be used to treat male and female urinary incontinence, in the form of stress, urge, mixed or overflow incontinence. Incontinence is a growing area of concern due to demographic factors such as aging populations as well as environmental factors that vary from location to location, globally.

These together with other objects of the invention, along with various features of novelty, which characterize the invention, are pointed out with particularity in the following specification. For a better understanding of the invention, its operating advantages and the specific objects attained by its uses, reference should be had to the accompanying drawing, descriptive matter and claims in which there is illustrated a preferred embodiment of the invention.

DETAILED DESCRIPTION OF INVENTION

Referring to the drawings in detail wherein like elements are indicated by like numerals, there is shown an exemplary method and apparatus of the present invention used for urinary incontinence. This does not limit the invention to this exemplary embodiment. Skilled practitioners in the art will recognize numerous other embodiments.

Figure 1:
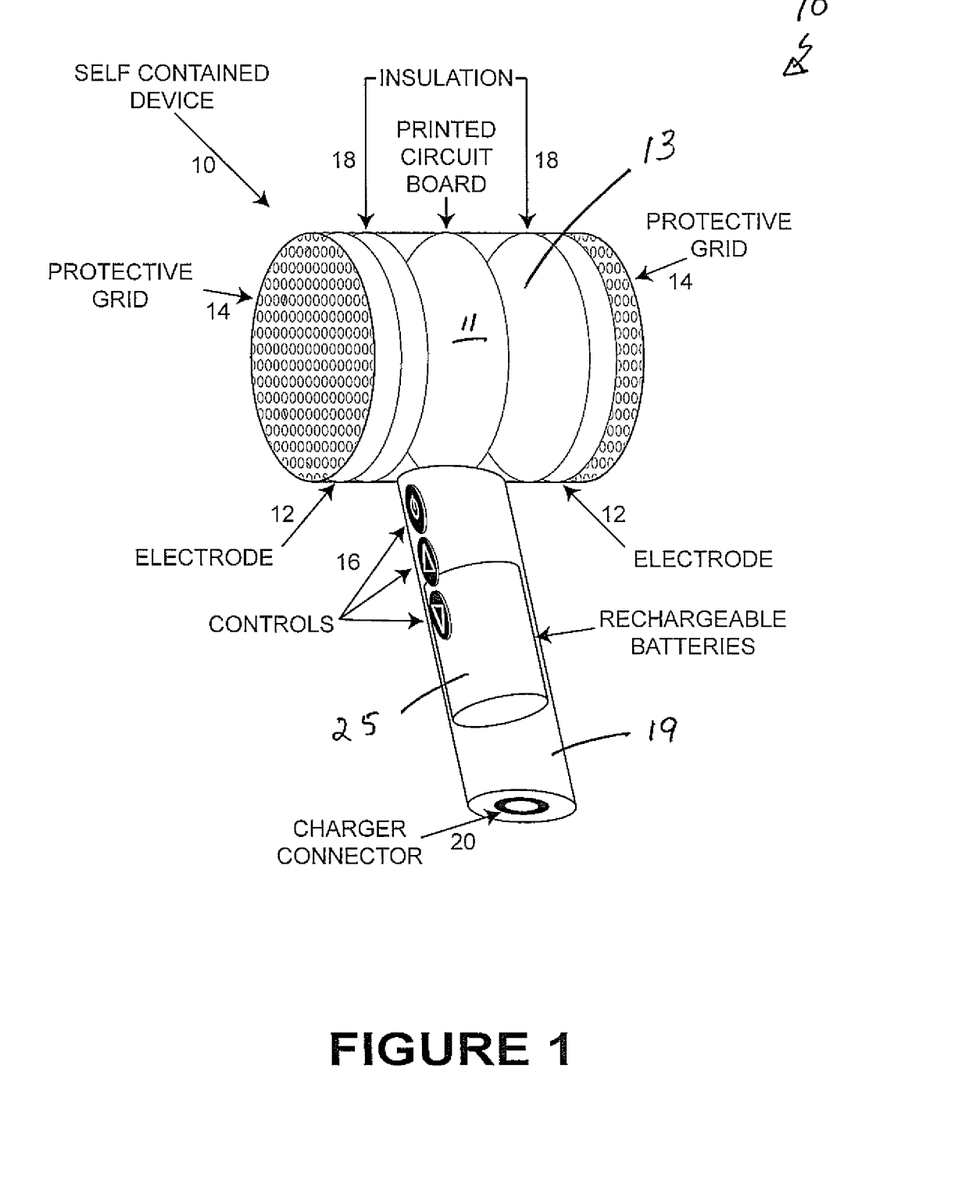
FIG. 1 is an illustrative drawing of the device of the present invention.
Figure 2:
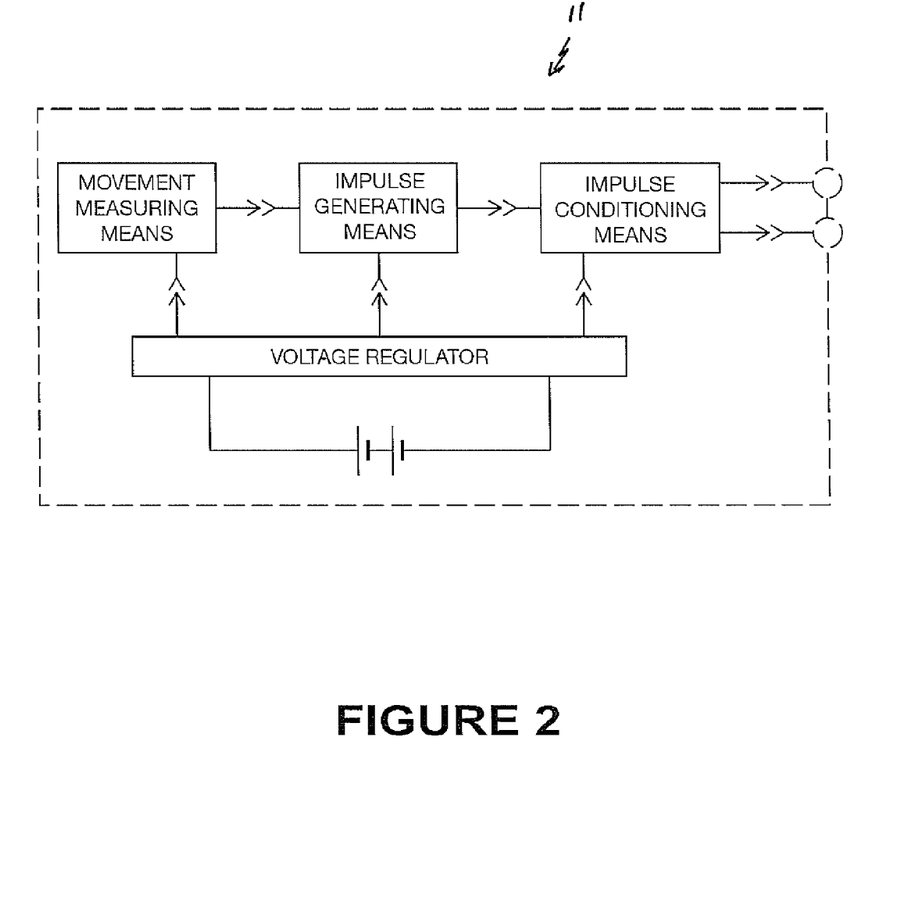
FIG. 2 is a block drawing of the electrical stimulation circuit design of the present invention.
Figure 3:
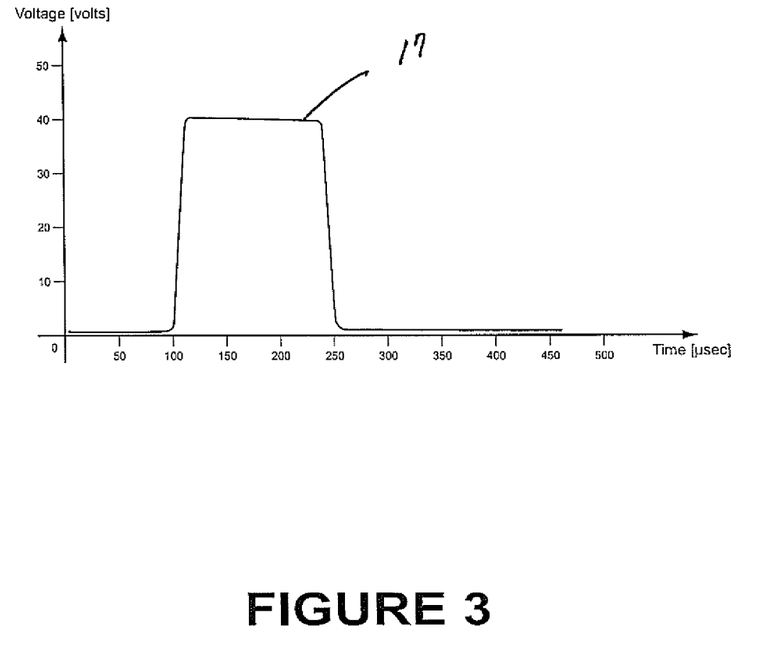
FIG. 3 is an illustrative oscilloscope screen representation of a single impulse waveform of the present invention.
Figure 4:
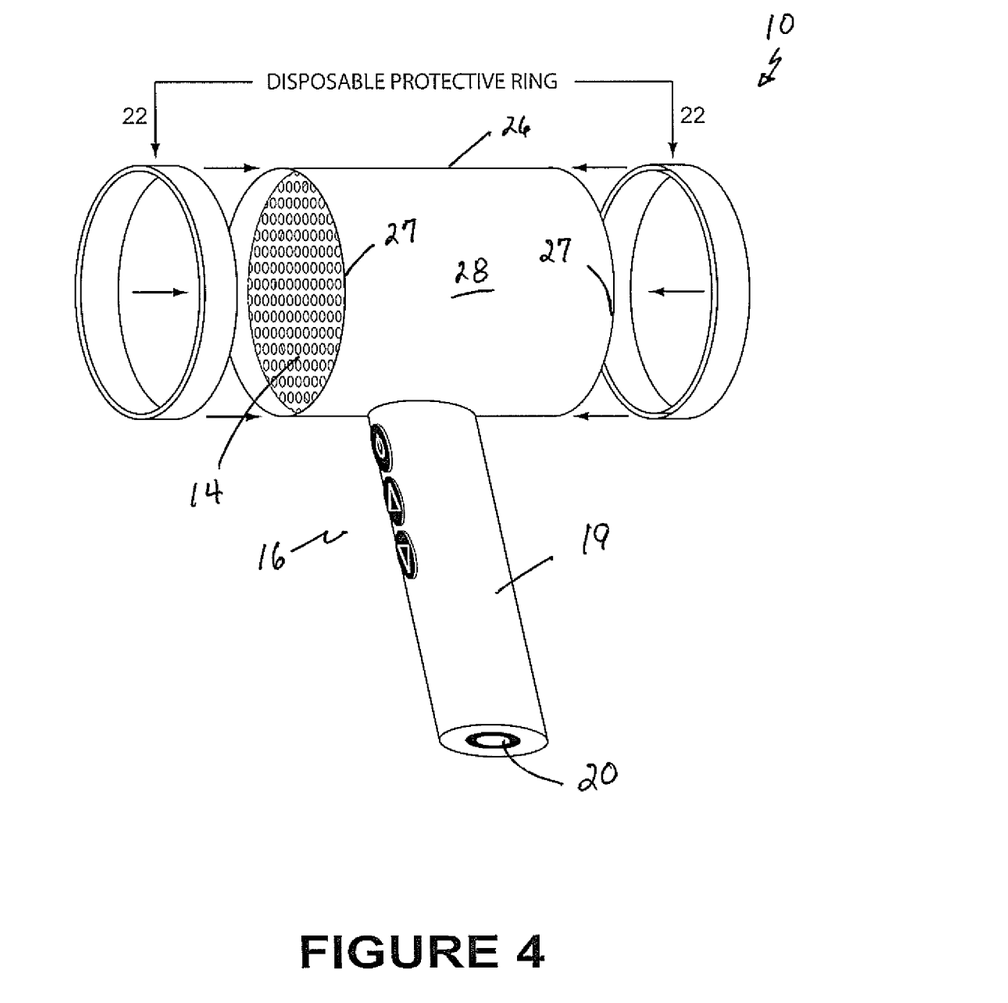
FIG. 4 is an illustrative drawing of a disposable insert into the device that enables use by multiple patients.

Referring more particularly to FIGS. 1 and 4, there is illustrated a self-contained, hand held wand 10 used in the present invention. The wand 10 is comprised of a cylindrical body 26 having two ends 27 and a cylindrical body 28 interconnecting the two ends 27. The cylindrical body and ends define a cylindrical body interior 13. The wand is further comprised of a hollow handle 19 protruding radially, preferably from the approximate center of the cylindrical body. The cylindrical body interior 13 contains electronic circuitry 11, said circuitry generating waveforms 17 of electrical impulses to two transmitting electrodes 12 on each end of the cylindrical body 26. The wand 10 has insulating disks 18 inserted between each electrode 12 and the electronic circuitry 11. The wand electronic circuitry 11 generates a pulse train at low frequencies, typically ranging from 1 to 120 Hz. The circuitry also has means to modulate the pulse duration. See, also, FIGS. 2 and 3.

The present invention wand 10 transmits the pulse train to a patient by means of the electrodes 12 positioned adjacent the skin of the patient directly over the treated muscle or over the nerve pathway leading to the respective muscle(s). The electrodes 12 are not placed directly on the skin of patients or users. An inert, protective grid 14 over each electrode 12 ensures this separation. For sanitary conditions, disposable inserts (protective rings) 22 are adapted to fit over each protective grid The wand handle 19 has controls 16 attached thereto, said controls electrically connected to the wand electronic circuitry 11 and providing start/stop control, pulse duration control and pulse train frequency control. The medical professional has only to position the device 10 appropriately over the desired area and, using the controls 16 commence delivery of the electrical stimulation for a pre-determined length of time. The handle 19 also has a chamber for a battery 25, which provides electrical power to the wand electronic circuitry 11. The wand cylindrical body and handle are sealed their interiors protected from fluids. The battery 25 is rechargeable from an external source through a charge connector 20 in the handle bottom. The electronic circuitry 11 may also include a memory unit for storage of multiple and different timing patterns for usage of the wand 10 to treat additional medical and non-medical conditions.

This method of stimulation in the exemplary situation differs from the prior art stimulation for treatment of urinary incontinence. In the standard application of the prior art, in order to cause effective muscle contractions in the pelvic area, the stimulation has to be delivered to patients or users by means of electrodes that are positioned and affixed to the pelvic area or inserted into body cavities. Such placement is often difficult to achieve is painful and/or uncomfortable for the patient or user, and difficult and painful to remove after treatment. These disadvantages are compounded when/if patients have significant physical challenges, for example, partial or complete paralysis.

Figure 6:
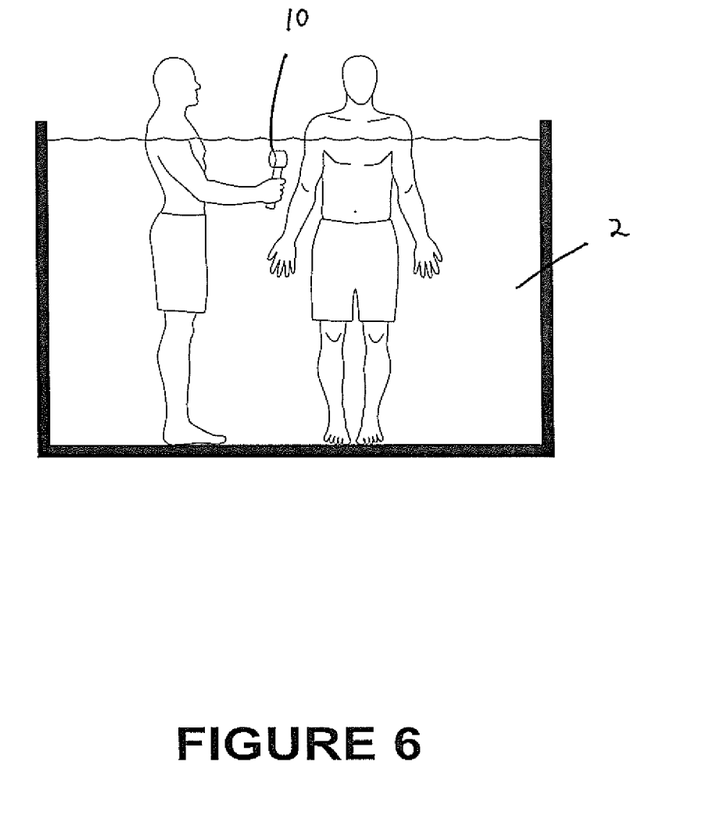
FIG. 6 is an illustrative drawing of a single patient treatment using the device of the present invention.
Figure 7:
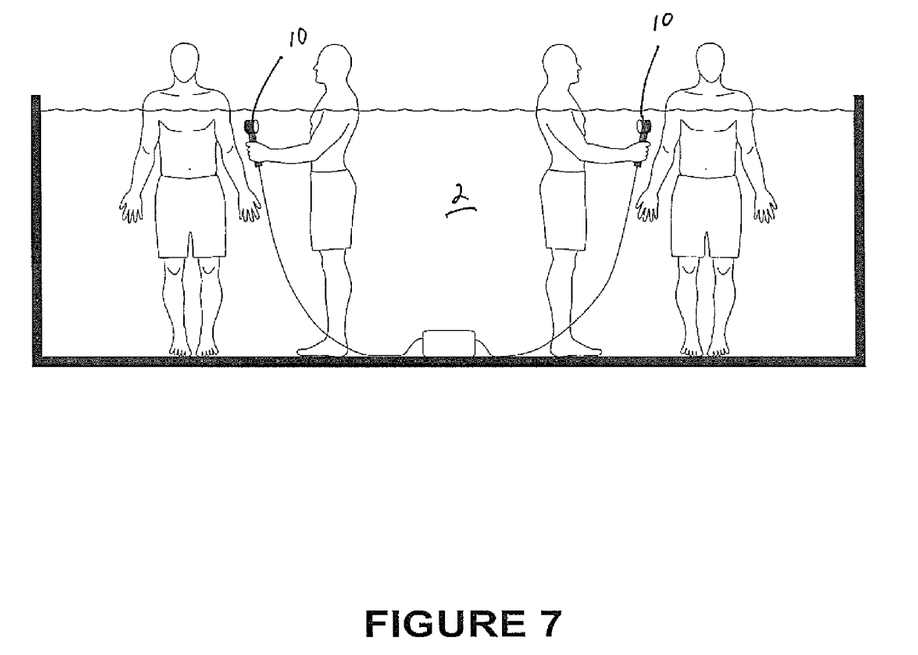
FIG. 7 is an illustrative drawing of multiple patient treatment using devices of the present invention.

The urinary incontinence treatment described above may be accomplished in a broad range of aqueous media 2, including fresh water, salt water and water that has been diluted with other aqueous or dissolvable components. Further, the treatment may be provided using a portable device 10 introduced completely or partially into the aqueous media or may be delivered with a device in which one electrode is stationary and the second electrode is contained in a portable device. See FIGS. 6 and 7. The present invention is different from prior art galvanic baths in that the aqueous medium is not charged. The stimulus radiates from the invention wand 10 through the aqueous media into the patient. There is no reaction with the aqueous medium. This permits electrical stimulation of a patient's muscle(s) and/or nerves while the patient is undergoing aquatic therapy.

The present invention is flexible in many aspects. The electrical signal transmission surface area is variable to accommodate patients of various ages and sizes. One or a multiple of patients FIGS. 6 and 7 may be treated simultaneously. The electrical stimulation signals can be any of the existing stimulation signals used by non-aqueous based electrical stimulation systems.

The present invention device is designed so that positive control 16 of the device by a medical professional or patient trained by a medical professional is required for electrical stimulation to commence and continue. Any irregular or abrupt motion of the device is detected and the electrical stimulation is immediately halted. User safety is also provided through insulation of the electronic circuitry) 1.

Figure 5:
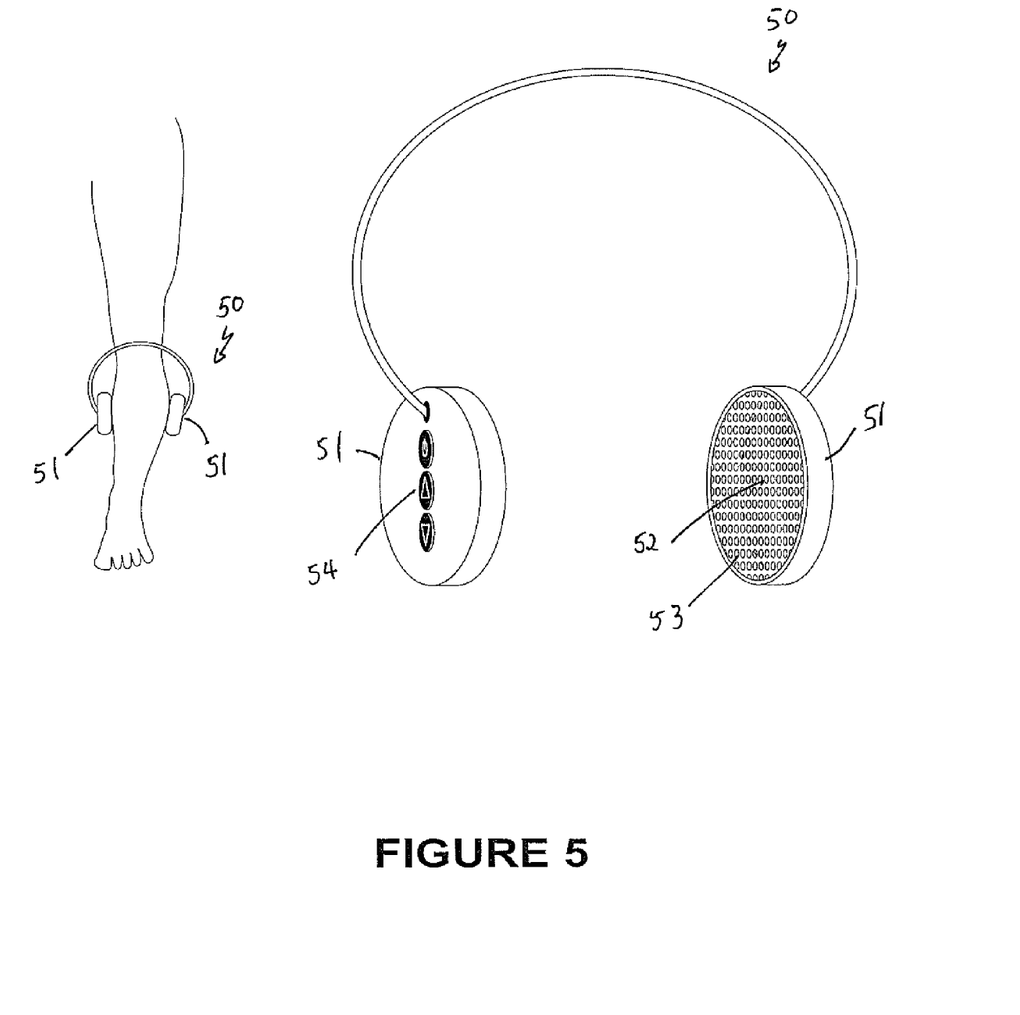
FIG. 5 is an illustrative drawing of a flexible device intended in this instance, but not limited to, venous thrombosis.

FIGS. 5, and 8-10 illustrate alternate embodiments of the invention. FIG. 5 illustrates an earmuff shaped device 50 comprised of two, interconnected, annular housings 51 terminating in a operative side in a transmitting electrode 52 with a protective grid 53. The operative sides of the housings may be placed over a limb to be treated. Electronic circuitry (not shown) is contained within one of the housings. The housing with the electronic circuitry has several controls 54 for control of the device operation.

Figure 8:
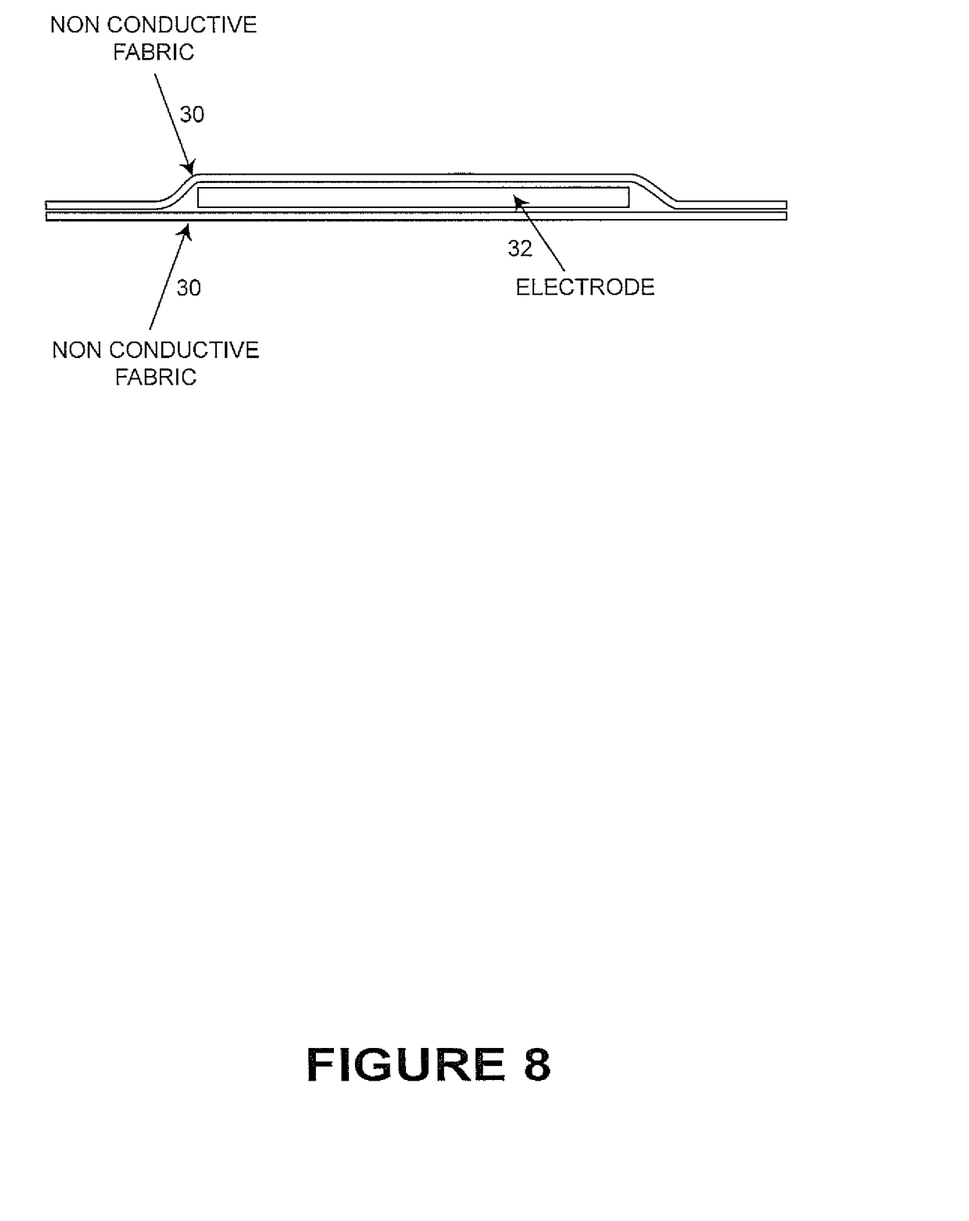
FIG. 8 is an illustrative drawing of a garment embedded/sealed electrode.
Figure 9:
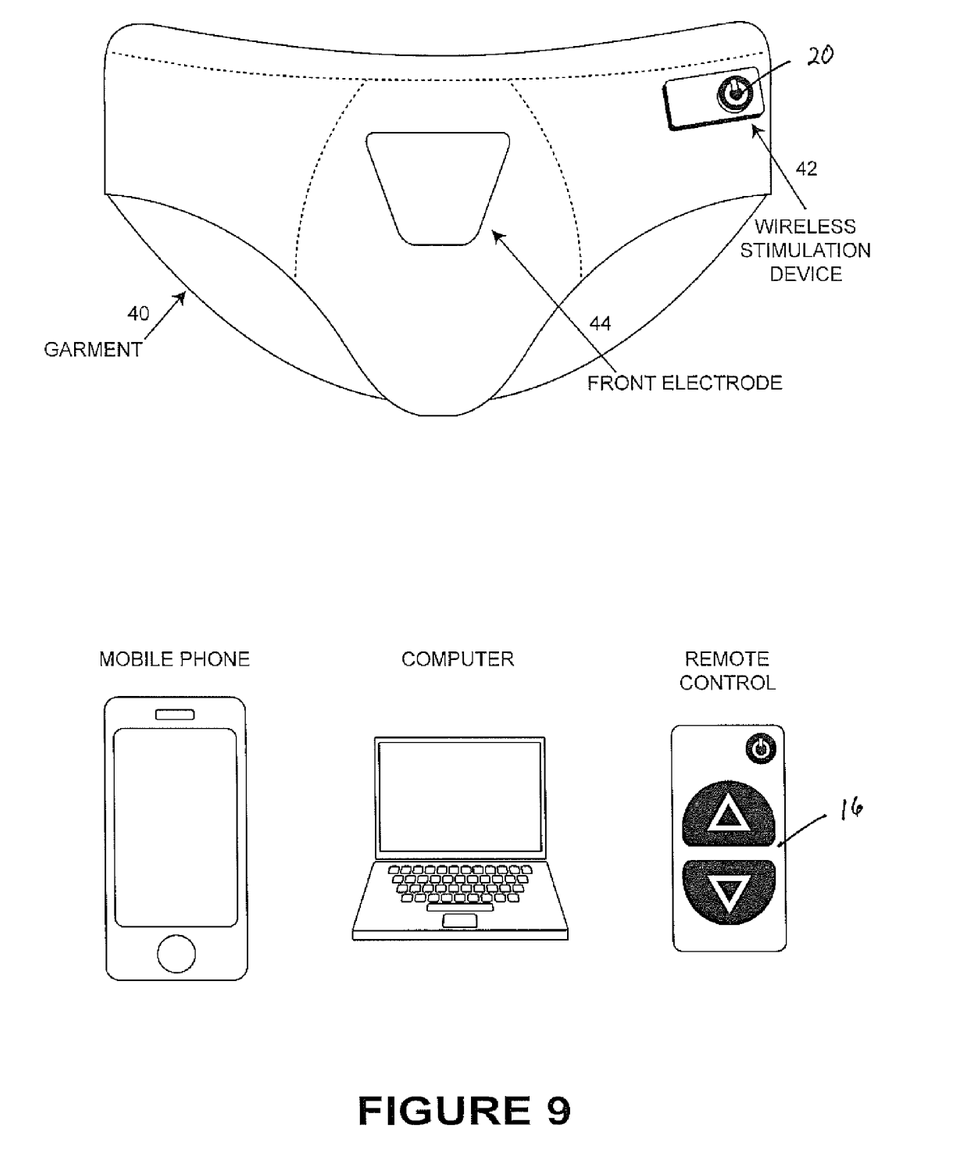
FIG. 9 is an illustrative drawing of a wireless configured garment.
Figure 10:
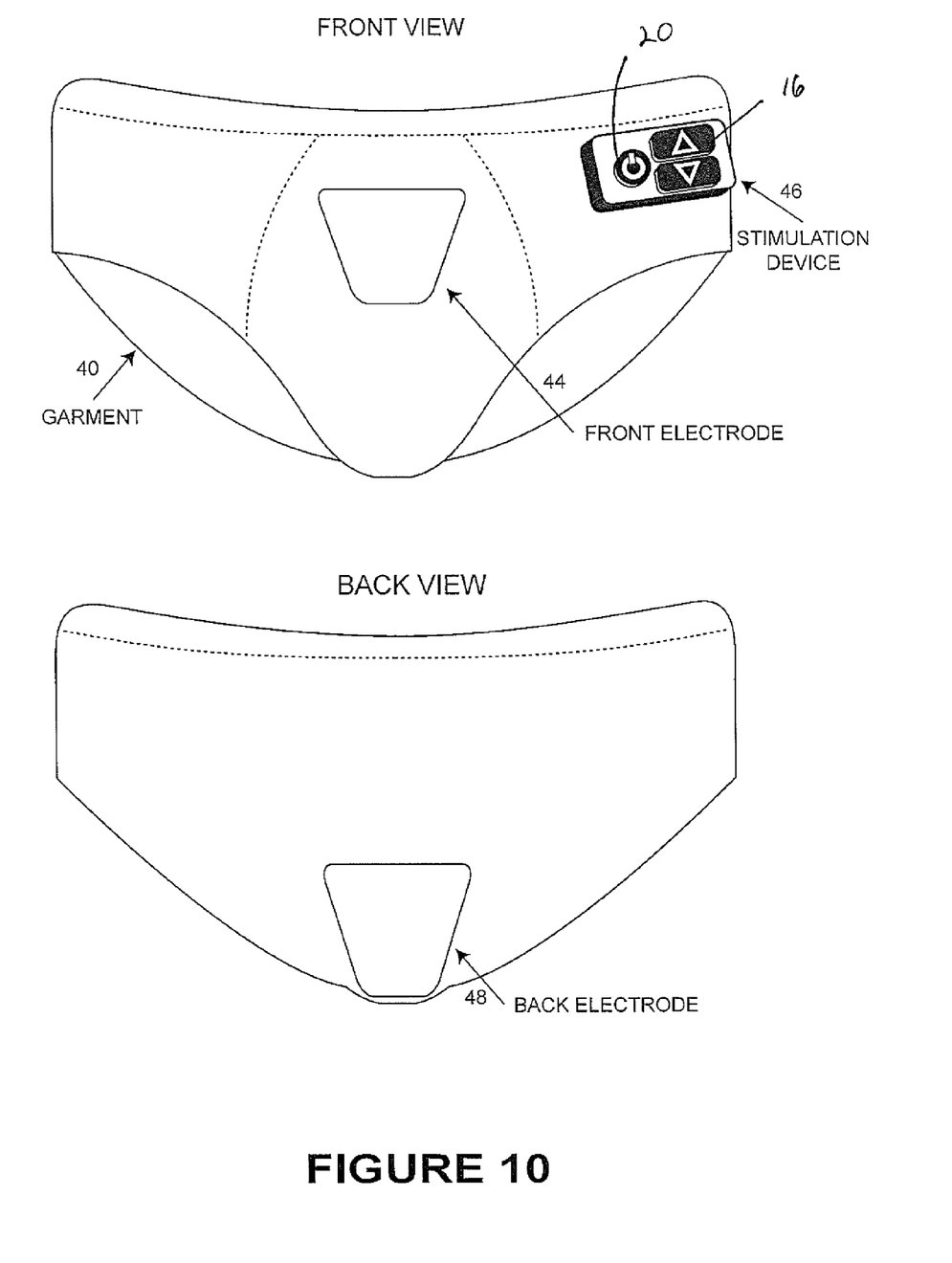
FIG. 10 is an illustrative drawing of a garment for the preferred embodiment.

FIGS. 8-10 illustrate an embodiment for use in a garment worn by a patient. FIG. 8 illustrates an electrode 32 sealed within a non conductive fabric. FIGS. 9 and 10 illustrate a garment 40 with a front electrode 44 and back electrode 48 contained within the front and rear of the garment. Stimulation devices 42 (wireless) and 46 (hard wired) are attached to the garments, each device having a charger port 20. The devices may have controls 16 directly on the device (FIG. 10) or remotely activated (FIG. 9).

It is understood that the above-described embodiments are merely illustrative of the application. Other embodiments may be readily devised by those skilled in the art which will embody the principles of the invention and fall within the spirit and scope thereof

We claim:

1. An apparatus for electrical muscle and nerve stimulation in aqueous media, comprising:
    a self-contained, hand held wand having a cylindrical body with two ends and comprising two transmitting electrodes on each end and a cylindrical wall interconnecting the two ends, said cylindrical wall and ends defining a cylindrical body interior;
    a hollow handle protruding radially from the approximate center of the cylindrical body;
    electronic circuitry in the cylindrical body interior, said electronic circuitry generating waveforms of electrical impulses to the two transmitting electrodes on each end of the cylindrical body;
    an insulating disk inserted between each electrode and the electronic circuitry;
    an inert, protective grid over each electrode;
    a power source within said handle, said power source electrically connected to and providing power to said electronic circuitry;
    a plurality of controls attached to the wand handle, said controls electrically connected to the wand electronic circuitry and providing start/stop control, pulse duration control and pulse train frequency control;
    wherein the wand cylindrical body and handle are sealed with their interiors protected from fluids.

2. An apparatus as recited in claim 1, wherein:
    the electronic circuitry in the wand generates a pulse train at low frequencies and transmits the pulse train to the electrodes; and
    the wand electronic circuitry has means to modulate each pulse duration.

3. An apparatus as recited in claim 2, further comprising:
    a protective grid over said electrodes and a plurality of disposable inserts in the form of protective rings, each adapted to fit over the protective grid.

4. An apparatus as recited in claim 3, further comprising a charge connector in the handle bottom and wherein the power source is rechargeable from an external source through the charge connector in the handle bottom.

5. An apparatus as recited in claim 4, wherein:
    the electronic circuitry in the wand includes a memory unit for storage of multiple and different timing patterns for usage of the wand.

6. An apparatus as recited in claim 5, wherein:
    the pulse train is in the range from 1 to 120 Hz.

* * * * *